United States Patent
McCann et al.

(10) Patent No.: US 6,300,471 B1
(45) Date of Patent: Oct. 9, 2001

(54) FSH-RELEASING PEPTIDES

(75) Inventors: Samuel M. McCann; Wen H. Yu, both of Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 09/089,522

(22) Filed: Jun. 3, 1998

Related U.S. Application Data

(60) Provisional application No. 60/092,112, filed on Jun. 4, 1997.

(51) Int. Cl.$^7$ ................................................. C07K 7/23
(52) U.S. Cl. ............................ 530/328; 514/15; 530/399
(58) Field of Search ................................. 530/327, 328, 530/399; 514/15, 2

(56) References Cited

U.S. PATENT DOCUMENTS

| | | | |
|---|---|---|---|
| 3,888,836 | 6/1975 | Veber et al. | 260/112.5 |
| 4,721,775 | 1/1988 | Folkers et al. | 530/313 |
| 4,973,577 | 11/1990 | Vale, Jr. et al. | 514/12 |

OTHER PUBLICATIONS

U.S. application 09/297,989, McCann et al., filed Mar. 11, 1999.
Schally, A. et al., Gonadotropin–releasing hormone: one polypeptide regulates secretion of luteninizing and follicle–stimulating hormones, Science, 173:1036–1038 (1971).
Schally, A. et al., Re–examination of porcine and bovine hypothalamic fractions for additional luteinizing hormone and follicle stimulating hormone–releasing activities, Endrocinology, 98:380–391 (1976).
Sower, S. et al., Primary structure and biological activity of a third gonadotropin–releasing hormone from lamprey brain, Endocrinology, 132:1125–1131 (1993).
Stopa, E. et al, Polygenic expression of gonadotropin–releasing hormone (GnRH) in Human?, Peptides, 9:419–423 (1988).

Yu, W. et al., Selective FSH–releasing activity of [D–Trp$^9$] GAP$_{1-13}$–comparison with gonadotropin–releasing abilities of analogs of GAP and natural LHRHs, Brain Res. Bull., 25:867–873 (1990).
Yu, W. et al., "A hypothalamic follicle–stimulating hormone–releasing decapeptide in the rat," Proc. Natl. Acad. Sci. USA, 94:9499–9503 (1997).
Dees, W. et al., Ethanol and the pulsatile release of luteinizing hormone, follicle stimulating hormone and prolactin in ovariectomized rats, Alcohol, 2:641–646 (1985).
Dhariwal, A. et al., Separation of follicle–stimulating hormone–releasing factor from luteinizing hormone–releasing factor, Endocrinology, 76:290–294 (1965).
Dhariwal, A. et al., Chromatographic behavior of follicle stimulating hormone–release factor on Sephadex and carboxy methyl cellulose, Neuroendocrinology, 2:294–303 (1967).
Igarashi, M. et al., A hypothalamic follicle stimulating hormone–releasing factor, Endocrinology, 74:446–452 (1964).
Lincoln, D., Gonadotropin–releasing hormone (GnRH): basic physiology, in L. DeGroot et al., Endocrinology, pp. 218–229 (1995).
Lumpkin, M. et al., Effect of destruction of the dorsal anterior hypothalamus on follicle–stimulating hormone secretion in the rat, Endocrinology, 115:2473–2480 (1984).
Lumpkin, M. Purification of FSH–releasing factor: Its dissimilarity from LHRH of mammalian, avian, and piscian origin, Brain Res. Bull., 18:175–178 (1987).
McCann, S. et al., Control of follicle–stimulating hormone and luteinizing hormone and release by hypothalamic peptides, Annals New York Academy of Sciences, 687:55–59 (1993).
Mizunuma, H., et al., Evidence for an FSH–releasing factor in the posterior portion of the rat median eminence, Life Sci., 33:2003–2009 (1983).
Samson, W. et al., Chromatographic and biologic analysis of ME and OVLT LHRH, Peptides, 1:97–102 (1980).

*Primary Examiner*—Christopher S. F. Low
*Assistant Examiner*—David Lukton
(74) *Attorney, Agent, or Firm*—John H. Runnels

(57) ABSTRACT

Lamprey LHRH-III is a potent FSH-releasing factor, and may be used to enhance fertility. Antagonists to lamprey LHRH-III may be used to inhibit fertility.

5 Claims, No Drawings

FSH-RELEASING PEPTIDES

The benefit of the Jun. 4, 1997 filing date of provisional application Ser. No. 06/092,112, is claimed under 35 U.S.C. § 119(e).

This invention was made with Government support under Grants DK43900 and MH51853 awarded by the National Institutes of Health. The Government has certain rights in this invention.

This invention pertains to compositions and methods for selectively stimulating or inhibiting the release of follicle-stimulating hormone from the anterior lobe of the pituitary gland.

The brain controls the release of gonadotropin hormones from the anterior pituitary gland. Two important gonadotropins are follicle-stimulating hormone (FSH) and luteinizing hormone (LH). FSH is critical for spermatogenesis and for ovarian follicle development, while LH is critical to androgen secretion in males, and estrogen secretion, ovulation, and formation of the corpus luteum ain females. A hormone with specific activity for releasing FSH but not LH could be used to increase fertility in humans or other animals, or to correct fertility problems caused by defective hypothalamic control of FSH secretion. Conversely, antisera or other antagonists to an FSH-specific releasing factor will inhibit FSH secretion, thereby inhibiting spermatogenesis in males, or inhibiting development of follicles and ovarian development in females, providing a new antifertility drug. It is also possible that very high doses of an FSH-specific releasing factor will inhibit FSH secretion, rather than stimulate it.

Prior indirect evidence has suggested that separate factors could be responsible for triggering the release of FSH and for triggering the release of LH in mammals. However, this hypothesis could not previously be confirmed, because no previous work successfully isolated a potent factor that selectively induces the release of FSH, but not LH. See McCann, S. et al., Control of follicle-stimulating hormone and luteinizing hormone release by hypothalamic peptides, Annals New York Academy of Sciences, 687:55–59, 1993; Dees, W. et al., Ethanol and the pulsatile release of luteinizing hormone, follicle stimulating hormone and prolactin in ovariectomized rats, Alcohol, 2:641–646, 1985; Dhariwal, A. et al., Separation of follicle-stimulating hormone-releasing factor from luteinizing hormone-releasing factor, Endocrinology, 76:290–294, 1965; Dhariwal, A. et al., Chromatographic behavior of follicle stimulating hormone-releasing factor on Sephadex and carboxy methyl cellulose, Neuroendocrinology, 2:294–303, 1967; Igarashi, M. et al., A hypothalamic follicle stimulating hormone-releasing factor, Endocrinology, 74:446–452, 1964; Lumpkin, M. et al., Effect of destruction of the dorsal anterior hypothalamus on follicle-stimulating hormone secretion in the rat, Endocrinology, 115:2473–2480, 1984; Samson, W. et al., Chromatographic and biologic analysis of ME and OVLT LHRH, Peptides, 1:97–102, 1980; Mizunuma, H., et al., Evidence for an FSH-releasing factor in the posterior portion of the rat median eminence, Life Sci., 33:2003–2009, 1983.

Luteinizing hormone releasing hormone (LHRH, also known as gonadotropin-releasing hormone, or GnRH) has both LH-releasing activity and FSH-releasing activity. See Schally, A. et al., Gonadotropin-releasing hormone: one polypeptide regulates secretion of luteinizing and follicle-stimulating hormones, Science, 173:1036–1038, 1971; and D. Lincoln, Gonadotropin-releasing hormone (GnRH): basic physiology, pp. 218–229 in L. DeGroot et al., Endocrinology, 1995. The latter states at page 218: "There is no convincing evidence for the existence of a separate and specific FSH-releasing hormone, although some components of the GNRH precursor and some ONRH analogues appear to differ in the degree to which they stimulate the secretion of the two gonadotropins."

Sower, S. et al., Primary structure and biological activity of a third gonadotropin-releasing hormone from lamprey brain, Endocrinology, 132:1125–1131, 1993 reported the structure of lamprey GnRH-III (referred to as l-LHRH-III in this specification), and reported that it stimulated estradiol and progesterone release from *Petromyzon marinus* (lamprey) ovaries. (Lampreys, jawless fish, are representatives of what is generally considered to be the most primitive of the extant classes of vertebrates.)

Lamprey l-LHRH-I has been reported to have relatively low activity in releasing either FSH or LH in rats. Yu, W. et al., Selective FSH-releasing activity of [D-Trp$^9$] GAP$_{1-13}$: comparison with gonadotropin-releasing abilities of analogs of GAP and natural LHRHs, Brain Res. Bull., 25:867–873, 1990.

Schally, A. et al., Re-examination of porcine and bovine hypothalamic fractions for additional luteinizing hormone and follicle stimulating hormone-releasing activities, Endocrinology, 98:380–391, 1976 reported that in vivo FSH-releasing activity could not be separated from LH-releasing activity from porcine hypothalami by fractionation on Sephadex, and concluded that there was only one gonadotropin-releasing hormone (GnRH).

By contrast, Lumpkin, M. et al., Purification of FSH-releasing factor: Its dissimilarity from LHRH of mammalian, avian, and piscian origin, Brain Res. Bull., 18:175–178, 1987 reported that FSH-releasing activity was separated from the LH-releasing activity in ovine hypothalami on Sephadex G-25, but did not isolate the factor causing FSH release.

Neurons that are immunopositive for l-LHRH-I have been identified in human hypothalami, projecting from the arcuate region to the median eminence. Stopa, E. et al, Polygenic expression of gonadotropin-releasing hormone (GnRH) in human?, Peptides, 9:419–423, 1988.

Lincoln, D., Luteinizing Hormone-Releasing Hormone, pp. 142–151 in DeGroot et al. (ed), Endocrinology, 1989, discloses various agonists and antagonists for mammalian LHRH.

W. Yu et al., "A hypothalamic follicle-stimulating hormone-releasing decapeptide in the rat," Proc. Natl. Acad. Sci. USA, 94:9499–9503, 1997 discloses some of the work reported in the present specification, but is not believed to constitute prior art.

U.S. Pat. No. 4,973,577 discloses a 28,000 dalton protein isolated from porcine follicular fluid that stimulates the release of FSH, but not of LH. This protein has a relatively slow onset of action, and is relatively difficult to synthesize. The protein was said to be a homodimer of two chains of 116 amino acid residues each, or 232 residues total.

U.S. Pat. No. 3,888,836 discloses a method for synthesizing mammalian LHRH. Mammalian LHRH causes increased serum levels of both LH and FSH.

U.S. Pat. No. 4,721,775 discloses certain peptides that non-selectively induce the secretion of both LH and FSH.

Attempts in our laboratory to purify FSH-releasing factor (FSH-RF) by fractionation of lamb hypothalami (discussed in some of the papers cited above) were successful only at certain seasons of the year, and even then we found that activity was lost after samples were stored at −20° C. (unpublished data). Thus our prior work did not successfully isolate or identify the putative FSH-releasing factor.

Other studies in our laboratory confirmed FSH-releasing activity by incubating stalk-median eminence (SME)-extracts in vitro with hemipituitaries from male rats. We confirmed the FSH-releasing activity of sheep and rat SME extracts in this assay, and found that the FSH-releasing activity emerged from columns of Sephadex G-25 just prior to emergence of LHRH, similar to results we had seen in an in vivo assay in ovariectomized, estrogen- and progesterone-blocked female rats. Even where we were able to extract crude or partially purified fractions showing selective FSH-releasing activity, that activity was relatively low compared to the activity of fractions with LH-releasing activity (unpublished data).

Our laboratory also screened known LHRH's from various species for selective FSH-releasing activity; and we also evaluated the activity of 25 analogs of LHRH in in vivo assays. (LHRH's from various species are disclosed in Lumpkin et al., 1987.) One analog was found to have only FSH-releasing activity, but its potency was very low, and the slope of its dose-response curve was flat. Of the known forms of LHRH from other species, we found that only chicken (c) LHRH-II had slightly preferential FSH-releasing activity in vivo (unpublished data).

We have unexpectedly discovered that l-LHRH-III is the long-sought FSH-releasing factor. This activity has been confirmed in vitro by incubation with hemi-anterior pituitaries of adult male rats. Following intravenous injection at the lowest dose tested to date (10 picomoles), this peptide produced an increase in FSH in vivo (P<0.01) within ten minutes, but no significant increase in LH. Such a selective effect has not previously been reported for any analog of mammalian LHRH.

dent's t-test was used to determine the significance of differences between two groups.

In Vitro Studies

After acclimatization for 5 or more days in the vivarium, male rats were killed by decapitation. Following removal of the posterior lobe, the anterior pituitary (AP) was bisected longitudinally, and each AP was incubated in a tube containing 0.5 ml Krebs-Ringer bicarbonate (5 mM ascorbic acid; pH 7.4) buffer (KRB) in an atmosphere of 95% $O_2$/5% $CO_2$ in a Dubnoff shaker (50 cycles per min) for a period of 60 min. Following this pre-incubation period, the APs were incubated for 3 hr in fresh KRB buffer alone (control), or in KRB containing one of various concentrations of synthetic mammalian (m)-LHRH, l-LHRH-III, l-LHRH-I, chicken (c)-LHRH-II, or salmon (s)-LHRH. The medium was then aspirated, and was stored frozen at −20° C. until radio-immunoassays (RIA) for FSH and LH were conducted. FSH and LH were measured using kits supplied by the National Institute of Arthritis Digestive Diabetes and Kidney Disease; hormone values were expressed in terms of NIH-rFSH-RP-2 and NIH-rLH-RP-3 standards. The experiments were repeated twice. The inter- and intra-assay coefficients of variation for FSH assays were 7.5% and 5.2%, respectively; and were 6.5% and 4.8% for LH assays.

In Vivo Studies

Female rats were ovariectomized under anesthesia with isoflurane 4 weeks prior to the in vivo experiments. Three days before blood sampling, each ovariectomized rat was injected subcutaneously with 50 μg estradiol benzoate (Sigma Chemical Co., St. Louis, Mo.) dissolved in 0.1 ml sesame oil, and 25 mg progesterone (Eli Lilly, Indianapolis, Ind.) dissolved in 0.5 ml sesame oil. One day prior to testing,

TABLE 1

Structure of Vertebrate LHRH's Tested

| | |
|---|---|
| Mammal (m-LHPH) | pGlu-His-Trp-Ser-<u>Tyr-Gly-Leu-Arg</u>-Pro-Gly-NH$_2$ (SEQ. ID NO. 2) |
| Lamprey III (l-LHRH-III) | pGlu-His-Trp-Ser-<u>His-Asp-Trp-Lys</u>-Pro-Gly-NH$_2$ (SEQ. ID NO. 1) |
| Lamprey I (l-LHRH-I) | pGlu-His-Tyr-Ser-Leu-Glu-Trp-Lys-Pro-Gly-NH$_2$ (SEQ. ID NO. 3) |
| Salmon (s-LHRH) | pGlu-His-Trp-Ser-Tyr-Gly-Trp-Leu-Pro-Gly-NH$_2$ (SEQ. ID NO. 4) |
| Chicken II (c-LHRH-II) | pGlu-His-Trp-Ser-His-Gly-Trp-Tyr-Pro-Gly-NH$_2$ (SEQ. ID NO. 5) |

General

Adult male and female Sprague-Dawley rats (Holtzmann, Madison, Wis.; 200–250 g) were housed two per cage under controlled conditions of temperature (23–25° C.) and lighting (on from 0500 to 1700 hr). The animals had free access to a pellet diet and to tap water.

The l-LHRH-III used in the experiments reported here was synthesized by standard solid-state peptide synthesis methods, and was purified to greater than 97% purity by preparative reverse-phase high performance liquid chromatography. All other peptides used were purchased from Peninsula Laboratories (Belmont, Calif.), except as otherwise noted.

The significance of differences among multiple groups was determined by analysis of variance, with subsequent Newman-Keuls multiple comparisons at each point. Stueach animal was implanted with a jugular-atrial catheter. On the morning of testing, polyethylene tubing (PE-50) was connected to the distal end of the jugular-atrial catheter on the rat's dorsum to facilitate blood sampling and intravenous injection. Animals were acclimatized one hour before initial blood samples were taken. Heparinized blood samples (5 ml) were collected just before, and at 10, 30, and 60 minutes after injection of 0.5 ml isotonic saline or l-LHRH-III (10 or 100 pmole) in 0.5 ml isotonic saline. After removal of each blood sample, an equal volume of isotonic saline was administered to maintain blood volume.

Effects of l-LHRH-I, l-LHRH-III, and Mammalian (m)-LHRH on FSH Release In Vitro

Lamprey l-LHRH-III caused FSH release in a dose-related fashion, with a minimal effective concentration (MEC) of $10^{-9}$ M (the lowest concentration tested) or lower, and a maximal effect at about $10^{-6}$ M. Thereafter, release of FSH levelled off through the highest concentration tested ($10^{-4}$ M).

Lamprey l-LHRH-I caused a small but statistically significant release of FSH at a concentration of $10^{-5}$ M; the amount of FSH released was significantly less than that caused by l-LHRH-III at the two concentrations tested ($10^{-6}$ and $10^{-5}$ M). By contrast, m-LHRH produced equivalent levels of FSH release at the two concentrations tested ($4\times10^{-9}$ and $2\times10^{-8}$ M) as compared to the levels induced by l-LHRH-III. See Table 2.

TABLE 2

| Group | FSH (ng/ml) |
| --- | --- |
| KRB (control) | 97.7 ± 20.4 |
| m-LHRH, $4 \times 10^{-9}$ M | ** 218.5 ± 35.7 |
| m-LHRH, $2 \times 10^{-8}$ M | ** 257.5 ± 42.4 |
| l-LHRH-III, $10^{-9}$ M | * 228.3 ± 52.5 |
| l-LHRH-III, $10^{-8}$ M | ** 255.7 ± 42.4 |
| l-LHRH-III, $10^{-7}$ M | *** 213.0 ± 17.9 |
| l-LHRH-III, $10^{-6}$ M | ** 278.2 ± 40.9 |
| l-LHRH-III, $10^{-5}$ M | ** 283.0 ± 60.8 |
| l-LHRH-III, $10^{-4}$ M | **** 368.6 ± 40.9 |
| l-LHRH-I, $10^{-6}$ M | * 164.0 ± 29.3 |
| l-LHRH-I, $10^{-5}$ M | ** 178.2 ± 17.0 | n = 6 in each case; * signifies $p < 0.05$;  signifies $p < 0.01$; * signifies $p < 0.001$; and **** signifies $p < 0.0001$ versus KRB control Effect of l-LHRH-I, l-LHRH-III, and m-LHRH on LH Release In Vitro In contrast to its effects on FSH release, l-LHRH-III had a much weaker effect on LH release. In fact, l-LHRH-III only caused the release of significant and comparable concentrations of LH at the three highest concentrations tested ($10^{-6}$–$10^{-4}$ M). We found that l-LHRH-I was inactive at the two concentrations tested ($10^{-6}$ and $10^{-5}$ M). Mammalian LHRH gave a dose-related stimulatory effect on LH release, and was active at the lowest concentration tested ($4\times10^{-9}$ M). See Table 3.

TABLE 3

| Group | LH (ng/ml) |
| --- | --- |
| KRB (control) | 139.3 ± 16.9 |
| m-LHRH, $4 \times 10^{-9}$ M | 183.1 ± 27.0 |
| m-LHRH, $2 \times 10^{-8}$ M | ** 262.0 ± 36.1 |
| l-LHRH-III, $10^{-9}$ M | 171.8 ± 27.3 |
| l-LHRH-III, $10^{-8}$ M | 165.7 ± 26.6 |
| l-LHRH-III, $10^{-7}$ M | 179.9 ± 28.4 |
| l-LHRH-III, $10^{-6}$ M | * 233.6 ± 33.8 |
| l-LHRH-III, $10^{-5}$ M | * 202.9 ± 31.2 |
| l-LHRH-III; $10^{-4}$ M | ** 236.6 ± 19.3 |
| l-LHRH-I, $10^{-6}$ M | 134.1 ± 23.2 |
| l-LHRH-I, $10^{-5}$ M | 120.4 ± 8.1 | n = 6 in each case; * signifies $p < 0.05$; ** signifies $p < 0.01$; versus KRB control Effects of Salmon and Chicken LHRH-II on Gonadotropin Release In Vitro Salmon (s)-LHRH stimulated the release of both FSH and LH at the two concentrations tested ($10^{-7}$ and $10^{-6}$ M). See Tables 4 and 5. Chicken (c) LHRH-II stimulated LH release at doses from $10^{-8}$ to $10^{-6}$ M, but the dose effect was not statistically significant. The c-LHRH-II had equivalent LH-releasing activity to that of m-LHRH, but l-LHRH-III showed no LH-releasing activity in this experiment. The c-LHRH-II only significantly increased FSH release at the highest concentration tested ($10^{-6}$ M). In this experiment, the MEC for l-LHRH-III for a statistically significant release of FSH was two orders of magnitude lower than that for c-LHRH-II.

TABLE 4

| Group | FSH (ng/ml) |
| --- | --- |
| KRB (control) | 157.5 ± 13.2 |
| m-LHRH, $2 \times 10^{-8}$ M | ** 320.5 ± 42.6 |
| l-LHRH-III, $10^{-9}$ M | 196.3 ± 21.2 |
| l-LHRH-III, $10^{-8}$ M | * 249.3 ± 31.3 |
| l-LHRH-III, $10^{-7}$ M | * 203.2 ± 16.4 |
| l-LHRH-III, $10^{-6}$ M | 215.0 ± 38.0 |
| c-LHRH-II, $10^{-8}$ M | 123.7 ± 18.0 |
| c-LHRH-II, $10^{-7}$ M | 209.3 ± 44.0 |
| c-LHRH-II, $10^{-6}$ M | *** 263.7 ± 17.8 |
| s-LHRH, $10^{-7}$ M | * 233.0 ± 37.4 |
| s-LHRH, $10^{-6}$ M | 203.2 ± 39.2 | n = 6 in each case; * signifies $p < 0.05$;  signifies $p < 0.01$; and * signifies $p < 0.001$ versus KRB control

TABLE 5

| Group | LH (ng/ml) |
| --- | --- |
| KRB (control) | 149.3 ± 17.0 |
| m-LHRH, $2 \times 10^{-8}$ M | * 214.7 ± 30.3 |
| l-LHRH-III, $10^{-9}$ M | 158.7 ± 10.2 |
| l-LHRH-III, $10^{-8}$ M | 163.2 ± 6.5 |
| l-LHRH-III, $10^{-7}$ M | 182.7 ± 13.7 |
| l-LHRH-III, $10^{-6}$ M | 176.0 ± 9.3 |
| c-LHRH-II, $10^{-8}$ M | * 199.3 ± 13.6 |
| c-LHRH-II, $10^{-7}$ M | * 216.3 ± 17.7 |
| c-LHRH-II, $10^{-6}$ M | * 239.0 ± 31.7 |
| s-LHRH, $10^{-7}$ M | * 230.8 ± 38.8 |
| s-LHRH, $10^{-6}$ M | 186.2 ± 13.6 | n = 6 in each case; * signifies $p < 0.05$ versus KRB control

Effects of l-LHRH-III on FSH and LH Release In Vivo

Saline-injected control animals experienced a significant decline in plasma FSH levels 10 minutes after injection, followed by a return to levels that did not differ significantly from pre-injection FSH levels by 30- and 60-minutes post-injection (data not shown).

Compared to the control animals, animals injected with the lowest dose of l-LHRH-III (10 pmole) showed a highly significant increase in plasma FSH 10 minutes after injection, an effect that vanished by 30 minutes post-injection. See Table 6. Increasing the dose of l-LHRH-III to 100 pmole produced a slightly greater effect at 10 minutes that was maintained 30 minutes after injection. Thus the 100 pmole dose caused a more prolonged effect than the 10 pmole dose.

TABLE 6

| Group | Change in FSH from baseline, 10 minutes post-injection (ng/ml) |
| --- | --- |
| saline | −3.85 ± 0.82 |
| l-LHRH-III, 10 pmole | ** −0.75 ± 0.37 |
| l-LHRH-III, 100 pmole | ** −0.43 ± 0.61 | n = 6 in each case, except n = 7 for l-LHRH-III, 100 pmole; ** signifies $p < 0.01$ versus saline control Injection of saline diluent produced a slight decrease in LH plasma concentration 10 minutes post-injection, an effect that continued for the duration of the experiment, but that was not statistically significant. Neither the 10 pmole nor the 100 pmole dose of l-LHRH-III produced a statistically Isignificant difference in LH levels versus saline control at any of the times measured. See Table 7.

TABLE 7

| Group | Change in LH from baseline, 10 minutes post-injection (ng/ml) |
|---|---|
| saline | −0.070 ± 0.122 |
| 1-LHRH-III, 10 pmole | −0.022 ± 0.078 |
| 1-LHRH-III, 100 pmole | 0.097 ± 0.077 | n = 6 in each case, except n = 7 for 1-LHRH-III, 100 pmole; the measured values were not significantly different from one another.

Thus l-LHRH-III caused the release of FSH in vivo, but not LH, at each of the two doses tested, 10 pmole and 100 pmole.

As these results have demonstrated, l-LHRH-III is the first highly specific and potent FSH-releasing peptide discovered. The l-LHRH-III behaves completely differently from the other polypeptides tested. We found that l-LHRH-I had minimal potency to release either FSH or LH. Salmon LHRH and chicken LHRH-II had low potency, and lacked specificity for FSH release. The in vivo assays using the other known vertebrate LHRH's showed that only one of them, c-LHRH-II, possessed even slight selectivity for FSH release.

We conclude that l-LHRH-III is a highly conserved peptide in vertebrates, and in particular that it or a closely related peptide is the mammalian peptide hormone responsible for the potent and specific release of FSH. If l-LHRH-III is not identical to the mammalian FSH-RF, the degree of homology between the two is quite high.

Mammalian m-LHRH and l-LHRH-III were approximately equipotent toward releasing FSH. The decreased potency of l-LHRH-III toward releasing LH is probably accounted for by the fact that l-LHRH-III only has 60% homology with m-LHRH (see Table 1). The differences in sequences are accounted for by the differing amino acids in positions 5–8, which presumably cause a drastic decrease in LH-releasing activity and an increase in FSH-releasing capabilities. It is probable that the tetrapeptide l-LHRH-III 5–8 binds to the active site of a putative specific FSH-RF receptor. Presumably, the FSH-RF receptor confers this specificity for FSH release, whereas the LHRH receptors stimulate the release of both hormones, albeit with a greater sensitivity for LH than FSH release. FSH-RF receptors may reside on gonadotropes that contain only FSH. LHRH receptors may cause release of both hormones from gonadotropes that contain both FSH and LH. LHRH receptors may also be located on gonadotropes that only contain LH.

Pulsatile gonadotropin release in the rat is characterized by simultaneous pulses of FSH and LH, by pulses of LH alone, and by pulses of FSH alone. We hypothesize that the first two types of pulses may be accounted for by LHRH, and the third by FSH-RF.

The discovery of FSH-RF has important implications for veterinary and human medicine. For example, treatment of farm animals with FSH-RF should lead to maturation of increased numbers of ovarian follicles and subsequent ovulations, leading to increased litter sizes. FSH-RF may be used as a drug to increase fertility in humans.

Related peptides are expected to be agonists or "superagonists" of l-LHRH-III. These agonists will be prepared and tested in similar assays. Particular examples include peptides in which (a) the $Asp^6$ amino acid residue has been replaced with another amino acid residue (naturally occurring or xenobiotic); or (b) in which the $Pro^9$ residue has been replaced with ProNHEt (prolyl ethyl amide) and the $Gly^{10}$—$NH_2$ has been deleted; or (c) both. Examples of such agonists include the following:

```
pGlu-His-Trp-Ser-His-Asp-Trp-Lys-(ProNHEt)              (SEQ. ID NO. 6)

pGlu-His-Trp-Ser-His-Ala-Trp-Lys-Pro-Gly-NH2            (SEQ. ID NO. 7)

pGlu-His-Trp-Ser-His-Ala-Trp-Lys-(PrONHEt)              (SEQ. ID NO. 8)

pGlu-His-Trp-Ser-His-(D-Ala)-Trp-Lys-Pro-Gly-NH2        (SEQ. ID NO. 9)

pGlu-His-Trp-Ser-His-(D-Ala)-Trp-Lys-(ProNHEt)          (SEQ. ID NO. 10)

pGlu-His-Trp-Ser-His-Leu-Trp-Lys-Pro-Gly-NH2            (SEQ. ID NO. 11)

pGlu-His-Trp-Ser-His-Leu-Trp-Lys-(PrONHEt)              (SEQ. ID NO. 12)

pGlu-His-Trp-Ser-His-(D)-Leu)-Trp-Lys-Pro-Gly-NH2       (SEQ. ID NO. 13)

pGlu-His-Trp-Ser-His-(D-Leu)-Trp-Lys-(ProNHEt)          (SEQ. ID NO. 14)

pGlu-His-Trp-Ser-His-(SerBuᵗ)-Trp-Lys-Pro-Gly-NH2       (SEQ. ID NO. 15)

pGlu-His-Trp-Ser-His-(SerBuᵗ)-Trp-Lys-(ProNHEt)         (SEQ. ID NO. 16)

pGlu-His-Trp-Ser-His-(D-SerBuᵗ)-Trp-Lys-Pro-Gly-NH2     (SEQ. ID NO. 17)

pGlu-His-Trp-Ser-His-(D-SerBuᵗ)-Trp-Lys-(ProNHEt)       (SEQ. ID NO. 18)

pGlu-His-Trp-Ser-His-Trp-Trp-Lys-Pro-Gly-NH2            (SEQ. ID NO. 19)

pGlu-His-Trp-Ser-His-Trp-Trp-Lys-(ProNHEt)              (SEQ. ID NO. 20)

pGlu-His-Trp-Ser-His-(D-Trp)-Trp-Lys-Pro-Gly-NH2        (SEQ. ID NO. 21)

pGlu-His-Trp-Ser-His-(D-Trp)-Trp-Lys-(ProNHEt)          (SEQ. ID NO. 22)
```

-continued

| | |
|---|---|
| pGlu-His-Trp-Ser-His-(His-Bzl)-Trp-Lys-Pro-Gly-NH$_2$ | (SEQ. ID NO. 23) |
| pGlu-His-Trp-Ser-His-(His-Bzl)-Trp-Lys-(ProNHEt) | (SEQ. ID NO. 24) |
| pGlu-His-Trp-Ser-His-(D-His-Bzl)-Trp-Lys-Pro-Gly-NH$_2$ | (SEQ. ID NO. 25) |
| pGlu-His-Trp-Ser-His-(D-His-Bzl)-Trp-Lys-(ProNHEt) | (SEQ. ID NO. 26) |
| pGlu-His-Trp-Ser-His-Nal(2)-Trp-Lys-Pro-Gly-NH$_2$ | (SEQ. ID NO. 27) |
| pGlu-His-Trp-Ser-His-Nal(2)-Trp-Lys-(ProNHEt) | (SEQ. ID NO. 28) |
| pGlu-His-Trp-Ser-His-(D-Nal(2))-Trp-Lys-Pro-Gly-NH$_2$ | (SEQ. ID NO. 29) |
| pGlu-His-Trp-Ser-His-(D-Nal(2))-Trp-Lys-(ProNHEt) | (SEQ. ID NO. 30) |
| pGlu-His-Trp-Ser-His-Nal(2)-Trp-Lys-Pro-(aza-Gly)-NH$_2$ | (SEQ. ID NO. 31) |
| pGlu-His-Trp-Ser-His-(D-Nal(2))-Trp-Lys-Pro-(aza-Gly)-NH$_2$ | (SEQ. ID NO. 32) |

Note: "(aza-Gly)—NH$_2$" in SEQ. ID NOs. 31 and 32 denotes —NH—NH—CONH$_2$.

Conversely, inhibitory analogs of the peptide, or antibodies against the peptide, may be used as potent antifertility drugs. Monoclonal or polyclonal antibodies against the peptide may be raised using standard techniques, initially conjugating the peptide to a carrier such as bovine serum albumin or keyhole limpet hemocyanin. Particular examples of antagonists include peptides in which one or more of residues 1, 2, 3, 6, and 10 have been replaced with another amino acid residue (naturally occurring or xenobiotic). Examples of such antagonists include the following:

| | |
|---|---|
| pGlu-(D-Phe)-Trp-Ser-His-(D-Ala)-Trp-Lys-Pro-Gly-NH$_2$ | (SEQ. ID NO. 33) |
| pGlu-(D-Phe)-(D-Trp)-Ser-His-(D-Trp)-Trp-Lys-Pro-Gly-NH$_2$ | (SEQ. ID NO. 34) |
| (D-pyro-Glu)-(D-Phe)-(D-Trp)-Ser-His-(D-Trp)-Trp-Lys-Pro-Gly-NH$_2$ | (SEQ. ID NO. 35) |
| (N-Ac-D-Phe)-(D-p-Cl-Phe)-(D-Trp)-Ser-His-(D-Trp)-Trp-Lys-Pro-Gly-NH$_2$ | (SEQ. ID NO. 36) |
| (N-Ac-D-p-Cl-Phe)-(Ac-D-p-Cl-Phe)-(D-Trp)-Ser-His-(D-Phe)-Trp-Lys-Pro-(D-Ala)-NH$_2$ | (SEQ. ID NO. 37) |
| (N-Ac-D-p-Cl-Phe)-(Ac-D-p-Cl-Phe)-(D-Trp)-Ser-His-(D-Arg)-Trp-Lys-Pro-(D-Ala)-NH$_2$ | (SEQ. ID NO. 38) |
| (N-Ac-D-Nal(2))-(p-F-D-Phe)-(D-Trp)-Ser-His-(D-Arg)-Trp-Lys-Pro-Gly-NH$_2$ | (SEQ. ID NO. 39) |
| (N-Ac-D-Nal(2))-(D-p-Cl-Phe)-(D-Trp)-Ser-His-(D-L-Arg-Et$^2$)-Trp-Lys-Pro-(D-Ala)-NH$_2$ | (SEQ. ID NO. 40) |
| (N-Ac-(D-Nal(2))-(D-p-Cl-Phe)-(D-3-Pal)-Ser-His-(D-Arg)-(D-Trp)-Lys-Pro-(D-Ala)-NH$_2$ | (SEQ. ID NO. 41) |

The effect of the peptide, its agonists, and its antagonists will be characterized in rats, and then in large mammals, such as sheep and pigs. After successful testing in large mammals, in vivo tests in primates will be conducted, in monkeys and in humans, in accordance with applicable laws and regulations.

The peptide, an agonist, or an antagonist, combined with a pharmaceutically acceptable carrier, may be administered to mammals, including humans, intravenously, subcutaneously, percutaneously, intramuscularly, or intranasally to increase fertility. It may also be administered to other vertebrates to increase fertility, for example sheep, cattle, pigs, chickens, turkeys, channel catfish, tilapia, and koi.

The active compound may be administered as a pharmaceutically acceptable salt, such as an acid addition salt; metal complex, e.g. with zinc, iron; or the like (which are considered salts for purposes herein). Illustrative of such acid addition salts are hydrochloride, hydrobromide, sulfate, phosphate, maleate, acetate, citrate, benzoate, succinate, malate, ascorbate, tartrate, and the like. Intravenous or other injections may be administered in isotonic saline, phosphate buffers, and the like.

The dosage will vary depending on the specific purpose for which the peptide is administered; appropriate dosages may readily be determined by those of skill in the art, an "effective amount" being that which elevates or depresses serum FSH levels by a statistically significant amount, or that which enhances or inhibits fertility to a statistically significant degree.

For example, a patient experiencing infertility of unknown cause may be tested for l-LHRH-III or FSH deficit through means otherwise known in the art, such as radioimmunoassay. Abnormally low FSH levels may indicate a deficiency in l-LHRH-III. Such patients may be tested for a positive response to exogenous l-LHRH-III. If administration of exogenous l-LHRH-III produces an increase in FSH, that finding indicates that administration of exogenous l-LHRH-III is a potential treatment for infertility.

As may prove most economical, the l-LHRH-III may be synthesized through any of various means known in the art, for example, synthesis on a solid-state peptide synthesizer, or expression of a cloned gene in E. coli.

The complete disclosures of all references cited in this specification are hereby incorporated by reference. In the event of an otherwise irreconcilable conflict, however, the present specification shall control.

We claim:

1. A method of altering the level of secretion of FSH in a vertebrate animal, comprising administering to the animal an effective amount of the peptide 1-LHRH-III (SEQ. ID NO. 1); wherein the amount of the peptide administered causes a selective change in the serum FSH level of the animal, but does not cause a proportional change in the serum LH level of the animal.

2. A method as recited in claim 1, wherein the animal is a mammal.

3. A method as recited in claim 2, wherein the animal is a human.

4. A method as recited in claim 3, wherein the human is a male.

5. A method as recited in claim 3, wherein the human is a female.

* * * * *

SEQUENCE LISTING (1) GENERAL INFORMATION:

(iii) NUMBER OF SEQUENCES: 41

(2) INFORMATION FOR SEQ ID NO:1:

(i) SEQUENCE CHARACTERISTICS:
      (A) LENGTH: 10 amino acids
      (B) TYPE: amino acid
      (D) TOPOLOGY: linear (ii) MOLECULE TYPE: peptide (ix) FEATURE:
      (D) OTHER INFORMATION:/note= "Xaa at 1 is pyro-Glu; Xaa
         at 10 is Gly-NH2"

(xi) SEQUENCE DESCRIPTION: SEQ ID NO:1:

Xaa His Trp Ser His Asp Trp Lys Pro Xaa
1               5                   10

(2) INFORMATION FOR SEQ ID NO:2:

(i) SEQUENCE CHARACTERISTICS:
      (A) LENGTH: 10 amino acids
      (B) TYPE: amino acid
      (D) TOPOLOGY: linear (ii) MOLECULE TYPE: peptide (ix) FEATURE:
      (D) OTHER INFORMATION:/note= "Xaa at 1 is pyro-Glu; Xaa
         at 10 is Gly-NH2"

(xi) SEQUENCE DESCRIPTION: SEQ ID NO:2:

Xaa His Trp Ser Tyr Gly Leu Arg Pro Xaa
1               5                   10

(2) INFORMATION FOR SEQ ID NO:3:

(i) SEQUENCE CHARACTERISTICS:
      (A) LENGTH: 10 amino acids
      (B) TYPE: amino acid
      (D) TOPOLOGY: linear (ii) MOLECULE TYPE: peptide (ix) FEATURE:
      (D) OTHER INFORMATION:/note= "Xaa at 1 is pyro-Glu; Xaa
         at 10 is Gly-NH2"

(xi) SEQUENCE DESCRIPTION: SEQ ID NO:3:

Xaa His Tyr Ser Leu Glu Trp Lys Pro Xaa
1               5                   10

(2) INFORMATION FOR SEQ ID NO:4:

(i) SEQUENCE CHARACTERISTICS:
      (A) LENGTH: 10 amino acids
      (B) TYPE: amino acid
      (D) TOPOLOGY: linear (ii) MOLECULE TYPE: peptide (ix) FEATURE:
      (D) OTHER INFORMATION:/note= "Xaa at 1 is pyro-Glu; Xaa
         at 10 is Gly-NH2"

(xi) SEQUENCE DESCRIPTION: SEQ ID NO:4:

```
Xaa His Trp Ser Tyr Gly Trp Leu Pro Xaa
1               5                   10

(2) INFORMATION FOR SEQ ID NO:5:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (D) OTHER INFORMATION:/note= "Xaa at 1 is pyro-Glu; Xaa
            at 10 is Gly-NH2"

(xi) SEQUENCE DESCRIPTION: SEQ ID NO:5:

Xaa His Trp Ser His Gly Trp Tyr Pro Xaa
1               5                   10

(2) INFORMATION FOR SEQ ID NO:6:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (D) OTHER INFORMATION:/note= "Xaa at 1 is pyro-Glu; Xaa
            at 9 is (ProNHEt)"

(xi) SEQUENCE DESCRIPTION: SEQ ID NO:6:

Xaa His Trp Ser His Asp Trp Lys Xaa
1               5

(2) INFORMATION FOR SEQ ID NO:7:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (D) OTHER INFORMATION:/note= "Xaa at 1 is pyro-Glu; Xaa
            at 10 is Gly-NH2"

(xi) SEQUENCE DESCRIPTION: SEQ ID NO:7:

Xaa His Trp Ser His Ala Trp Lys Pro Xaa
1               5                   10

(2) INFORMATION FOR SEQ ID NO:8:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (D) OTHER INFORMATION: /note= "Xaa at 1 is pyro-Glu;
            Xaa at 9 is (ProNHEt)"

(xi) SEQUENCE DESCRIPTION: SEQ ID NO:8:

Xaa His Trp Ser His Ala Trp Lys Xaa
1               5
```

```
(2) INFORMATION FOR SEQ ID NO:9:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (D) OTHER INFORMATION: /note= "Xaa at 1 is pyro-Glu;
            Xaa at 6 is (D-Ala); Xaa at 10 is Gly-NH2"

(xi) SEQUENCE DESCRIPTION: SEQ ID NO:9:

Xaa His Trp Ser His Xaa Trp Lys Pro Xaa
1               5                   10

(2) INFORMATION FOR SEQ ID NO:10:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (D) OTHER INFORMATION: /note= "Xaa at 1 is pyro-Glu;
            Xaa at 6 is (D-Ala); Xaa at 9 is (ProNHEt)"

(xi) SEQUENCE DESCRIPTION: SEQ ID NO:10:

Xaa His Trp Ser His Xaa Trp Lys Xaa
1               5

(2) INFORMATION FOR SEQ ID NO:11:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (D) OTHER INFORMATION:/note= "Xaa at 1 is pyro-Glu; Xaa
            at 10 is Gly-NH2"

(xi) SEQUENCE DESCRIPTION: SEQ ID NO:11:

Xaa His Trp Ser His Leu Trp Lys Pro Xaa
1               5                   10

(2) INFORMATION FOR SEQ ID NO:12:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (D) OTHER INFORMATION: /note= "Xaa at 1 is pyro-Glu;
            Xaa at 9 is (ProNHEt)"

(xi) SEQUENCE DESCRIPTION: SEQ ID NO:12:

Xaa His Trp Ser His Leu Trp Lys Xaa
1               5

(2) INFORMATION FOR SEQ ID NO:13:
```

(i) SEQUENCE CHARACTERISTICS:
            (A) LENGTH: 10 amino acids
            (B) TYPE: amino acid
            (D) TOPOLOGY: linear (ii) MOLECULE TYPE: peptide (ix) FEATURE:
            (D) OTHER INFORMATION: /note= "Xaa at 1 is pyro-Glu;
                Xaa at 6 is (D-Leu); Xaa at 10 is Gly-NH2"

(xi) SEQUENCE DESCRIPTION: SEQ ID NO:13:

Xaa His Trp Ser His Xaa Trp Lys Pro Xaa
1               5                   10

(2) INFORMATION FOR SEQ ID NO:14:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (ix) FEATURE:
            (D) OTHER INFORMATION: /note= "Xaa at 1 is pyro-Glu;
                Xaa at 6 is (D-Leu); Xaa at 9 is (ProNHEt)"

(xi) SEQUENCE DESCRIPTION: SEQ ID NO:14:

Xaa His Trp Ser His Xaa Trp Lys Xaa
1               5

(2) INFORMATION FOR SEQ ID NO:15:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (ix) FEATURE:
            (D) OTHER INFORMATION: /note= "Xaa at 1 is pyro-Glu;
                Xaa at 6 is (SerBut); Xaa at 10 is Gly-NH2"

(xi) SEQUENCE DESCRIPTION: SEQ ID NO:15:

Xaa His Trp Ser His Xaa Trp Lys Pro Xaa
1               5                   10

(2) INFORMATION FOR SEQ ID NO:16:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (ix) FEATURE:
            (D) OTHER INFORMATION: /note= "Xaa at 1 is pyro-Glu;
                Xaa at 6 is (SerBut); Xaa at 9 is (ProNHEt)"

(xi) SEQUENCE DESCRIPTION: SEQ ID NO:16:

Xaa His Trp Ser His Xaa Trp Lys Xaa
1               5

(2) INFORMATION FOR SEQ ID NO:17:

(i) SEQUENCE CHARACTERISTICS:
            (A) LENGTH: 10 amino acids (B) TYPE: amino acid
            (D) TOPOLOGY: linear (ii) MOLECULE TYPE: peptide (ix) FEATURE:
            (D) OTHER INFORMATION: /note= "Xaa at 1 is pyro-Glu;
                Xaa at 6 is (D-SerBut); Xaa at 10 is Gly-NH2"

(xi) SEQUENCE DESCRIPTION: SEQ ID NO:17:

Xaa His Trp Ser His Xaa Trp Lys Pro Xaa
1               5                   10

(2) INFORMATION FOR SEQ ID NO:18:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (ix) FEATURE:
            (D) OTHER INFORMATION: /note= "Xaa at 1 is pyro-Glu;
                Xaa at 6 is (D-SerBut); Xaa at 9 is (ProNHEt)"

(xi) SEQUENCE DESCRIPTION: SEQ ID NO:18:

Xaa His Trp Ser His Xaa Trp Lys Xaa
1               5

(2) INFORMATION FOR SEQ ID NO:19:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (ix) FEATURE:
            (D) OTHER INFORMATION:/note= "Xaa at 1 is pyro-Glu; Xaa
                at 10 is Gly-NH2"

(xi) SEQUENCE DESCRIPTION: SEQ ID NO:19:

Xaa His Trp Ser His Trp Trp Lys Pro Xaa
1               5                   10

(2) INFORMATION FOR SEQ ID NO:20:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (ix) FEATURE:
            (D) OTHER INFORMATION: /note= "Xaa at 1 is pyro-Glu;
                Xaa at 9 is (ProNHEt)"

(xi) SEQUENCE DESCRIPTION: SEQ ID NO:20:

Xaa His Trp Ser His Trp Trp Lys Xaa
1               5

(2) INFORMATION FOR SEQ ID NO:21:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (ix) FEATURE:
            (D) OTHER INFORMATION: /note= "Xaa at 1 is pyro-Glu;
                Xaa at 6 is (D-Trp); Xaa at 10 is Gly-NH2"

(xi) SEQUENCE DESCRIPTION: SEQ ID NO:21:

Xaa His Trp Ser His Xaa Trp Lys Pro Xaa
1               5                   10

(2) INFORMATION FOR SEQ ID NO:22:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (ix) FEATURE:
            (D) OTHER INFORMATION: /note= "Xaa at 1 is pyro-Glu;
                Xaa at 6 is (D-Trp); Xaa at 9 is (ProNHEt)"

(xi) SEQUENCE DESCRIPTION: SEQ ID NO:22:

Xaa His Trp Ser His Xaa Trp Lys Xaa
1               5

(2) INFORMATION FOR SEQ ID NO:23:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (ix) FEATURE:
            (D) OTHER INFORMATION: /note= "Xaa at 1 is pyro-Glu;
                Xaa at 6 is (His-Bzl); Xaa at 10 is Gly-NH2"

(xi) SEQUENCE DESCRIPTION: SEQ ID NO:23:

Xaa His Trp Ser His Xaa Trp Lys Pro Xaa
1               5                   10

(2) INFORMATION FOR SEQ ID NO:24:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (ix) FEATURE:
            (D) OTHER INFORMATION: /note= "Xaa at 1 is pyro-Glu;
                Xaa at 6 is (His-Bzl); Xaa at 9 is (ProNHEt)"

(xi) SEQUENCE DESCRIPTION: SEQ ID NO:24:

Xaa His Trp Ser His Xaa Trp Lys Xaa
1               5

(2) INFORMATION FOR SEQ ID NO:25:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (ix) FEATURE:

(D) OTHER INFORMATION: /note= "Xaa at 1 is pyro-Glu;
                Xaa at 6 is (D-His-Bzl); Xaa at 10 is Gly-NH2"

(xi) SEQUENCE DESCRIPTION: SEQ ID NO:25:

Xaa His Trp Ser His Xaa Trp Lys Pro Xaa
1               5                   10

(2) INFORMATION FOR SEQ ID NO:26:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
            (D) OTHER INFORMATION: /note= "Xaa at 1 is pyro-Glu;
                Xaa at 6 is (D-His-Bzl); Xaa at 9 is (ProNHEt)"

(xi) SEQUENCE DESCRIPTION: SEQ ID NO:26:

Xaa His Trp Ser His Xaa Trp Lys Xaa
1               5

(2) INFORMATION FOR SEQ ID NO:27:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
            (D) OTHER INFORMATION: /note= "Xaa at 1 is pyro-Glu;
                Xaa at 6 is Nal(2); Xaa at 10 is Gly-NH2"

(xi) SEQUENCE DESCRIPTION: SEQ ID NO:27:

Xaa His Trp Ser His Xaa Trp Lys Pro Xaa
1               5                   10

(2) INFORMATION FOR SEQ ID NO:28:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
            (D) OTHER INFORMATION: /note= "Xaa at 1 is pyro-Glu;
                Xaa at 6 is Nal(2); Xaa at 9 is (ProNHEt)"

(xi) SEQUENCE DESCRIPTION: SEQ ID NO:28:

Xaa His Trp Ser His Xaa Trp Lys Xaa
1               5

(2) INFORMATION FOR SEQ ID NO:29:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
            (D) OTHER INFORMATION: /note= "Xaa at 1 is pyro-Glu;
                Xaa at 6 is (D-Nal(2)); Xaa at 10 is Gly-NH2"

(xi) SEQUENCE DESCRIPTION: SEQ ID NO:29:

Xaa His Trp Ser His Xaa Trp Lys Pro Xaa
1               5                   10

(2) INFORMATION FOR SEQ ID NO:30:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (D) OTHER INFORMATION: /note= "Xaa at 1 is pyro-Glu;
            Xaa at 6 is (D-Nal(2)); Xaa at 9 is (ProNHEt)"

(xi) SEQUENCE DESCRIPTION: SEQ ID NO:30:

Xaa His Trp Ser His Xaa Trp Lys Xaa
1               5

(2) INFORMATION FOR SEQ ID NO:31:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (D) OTHER INFORMATION: /note= "Xaa at 1 is pyro-Glu;
            Xaa at 6 is Nal(2); Xaa at 10 is (aza-Gly)"

(xi) SEQUENCE DESCRIPTION: SEQ ID NO:31:

Xaa His Trp Ser His Xaa Trp Lys Pro Xaa
1               5                   10

(2) INFORMATION FOR SEQ ID NO:32:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (D) OTHER INFORMATION: /note= "Xaa at 1 is pyro-Glu;
            Xaa at 6 is (D-Nal(2)); Xaa at 10 is (aza-Gly)"

(xi) SEQUENCE DESCRIPTION: SEQ ID NO:32:

Xaa His Trp Ser His Xaa Trp Lys Pro Xaa
1               5                   10

(2) INFORMATION FOR SEQ ID NO:33:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (D) OTHER INFORMATION: /note= "Xaa at 1 is pyro-Glu;
            Xaa at 2 is (D-Phe); Xaa at 6 is (D-Ala); Xaa at 10 is
            Gly-NH2"

(xi) SEQUENCE DESCRIPTION: SEQ ID NO:33:

```
Xaa Xaa Trp Ser His Xaa Trp Lys Pro Xaa
1               5                   10

(2) INFORMATION FOR SEQ ID NO:34:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (D) OTHER INFORMATION: /note= "Xaa at 1 is pyro-Glu;
            Xaa at 2 is (D-Phe); Xaa at 3 is (D-Trp); Xaa at 6 is
            (D-Trp); Xaa at 10 is Gly-NH2"

(xi) SEQUENCE DESCRIPTION: SEQ ID NO:34:

Xaa Xaa Xaa Ser His Xaa Trp Lys Pro Xaa
1               5                   10

(2) INFORMATION FOR SEQ ID NO:35:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (D) OTHER INFORMATION: /note= "Xaa at 1 is
            (D-pyro-Glu); Xaa at 2 is (D-Phe); Xaa at 3 is (D-Trp); Xaa
            at 6 is (D-Trp); Xaa at 10 is Gly-NH2"

(xi) SEQUENCE DESCRIPTION: SEQ ID NO:35:

Xaa Xaa Xaa Ser His Xaa Trp Lys Pro Xaa
1               5                   10

(2) INFORMATION FOR SEQ ID NO:36:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (D) OTHER INFORMATION: /note= "Xaa at 1 is
            (N-Ac-D-Phe); Xaa at 2 is (D-p-Cl-Phe); Xaa at 3 is (D-Trp);
            Xaa at 6 is (D-Trp); Xaa at 10 is Gly-NH2"

(xi) SEQUENCE DESCRIPTION: SEQ ID NO:36:

Xaa Xaa Xaa Ser His Xaa Trp Lys Pro Xaa
1               5                   10

(2) INFORMATION FOR SEQ ID NO:37:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (D) OTHER INFORMATION: /note= "Xaa at 1 is
            (N-Ac-D-p-Cl-Phe); Xaa at 2 is (Ac-D-p-Cl-Phe); Xaa at 3 is
            (D-Trp); Xaa at 6 is (D-Phe); Xaa at 10 is (D-Ala-NH2)"

(xi) SEQUENCE DESCRIPTION: SEQ ID NO:37:
```

```
Xaa Xaa Xaa Ser His Xaa Trp Lys Pro Xaa
1               5                   10
```

(2) INFORMATION FOR SEQ ID NO:38:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (D) OTHER INFORMATION: /note= "Xaa at 1 is
        (N-Ac-D-p-Cl-Phe); Xaa at 2 is (Ac-D-p-Cl-Phe); Xaa at 3 is
        (D-Trp); Xaa at 6 is (D-Arg); Xaa at 10 is (D-Ala-NH2)"

(xi) SEQUENCE DESCRIPTION: SEQ ID NO:38:

```
Xaa Xaa Xaa Ser His Xaa Trp Lys Pro Xaa
1               5                   10
```

(2) INFORMATION FOR SEQ ID NO:39:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (D) OTHER INFORMATION: /note= "Xaa at 1 is
        (N-Ac-D-Nal(2)); Xaa at 2 is (p-F-D-Phe); Xaa at 3 is
        (D-Trp); Xaa at 6 is (D-Arg); Xaa at 10 is Gly-NH2"

(xi) SEQUENCE DESCRIPTION: SEQ ID NO:39:

```
Xaa Xaa Xaa Ser His Xaa Trp Lys Pro Xaa
1               5                   10
```

(2) INFORMATION FOR SEQ ID NO:40:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (D) OTHER INFORMATION: /note= "Xaa at 1 is
        (N-Ac-D-Nal(2)); Xaa at 2 is (D-p-Cl-Phe); Xaa at 3 is
        (D-Trp); Xaa at 6 is (D-L-Arg-Et2); Xaa at 10 is (D-Ala-NH2)"

(xi) SEQUENCE DESCRIPTION: SEQ ID NO:40:

```
Xaa Xaa Xaa Ser His Xaa Trp Lys Pro Xaa
1               5                   10
```

(2) INFORMATION FOR SEQ ID NO:41:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (D) OTHER INFORMATION:/note= "Xaa at 1 is
        (N-Ac-D-Nal(2)); Xaa at 2 is (D-p-Cl-Phe); Xaa at 3 is
        (D-3-Pal); Xaa at 6 is (D-Arg); Xaa at 7 is (D-Trp); Xaa at
        10 is (D-Ala-NH2)"

-continued (xi) SEQUENCE DESCRIPTION: SEQ ID NO:41:

Xaa Xaa Xaa Ser His Xaa Xaa Lys Pro Xaa
1               5                   10